(12) United States Patent
Lacoste et al.

(10) Patent No.: US 7,753,944 B2
(45) Date of Patent: Jul. 13, 2010

(54) ULTRASONIC IMAGING AND TREATMENT PROBE HAVING AN ASYMMETRIC FOCAL ZONE

(75) Inventors: Francois Lacoste, Paris (FR); Olivier Esnault, Paris (FR)

(73) Assignee: Technomed Medical Systems S.A., Vaux en Velin (FR)

( * ) Notice: Subject to any disclaimer, the term of this patent is extended or adjusted under 35 U.S.C. 154(b) by 884 days.

(21) Appl. No.: 10/482,515

(22) PCT Filed: Jul. 5, 2002

(86) PCT No.: PCT/FR02/02367

§ 371 (c)(1),
(2), (4) Date: Aug. 5, 2004

(87) PCT Pub. No.: WO03/008041

PCT Pub. Date: Jan. 30, 2003

(65) Prior Publication Data

US 2004/0254620 A1 Dec. 16, 2004

(30) Foreign Application Priority Data

Jul. 13, 2001 (FR) .................................. 01 09370

(51) Int. Cl.
*A61F 7/12* (2006.01)
(52) U.S. Cl. ....................................................... 607/96
(58) Field of Classification Search ................. 600/459;
607/96; 601/4
See application file for complete search history.

(56) References Cited

U.S. PATENT DOCUMENTS

| 4,858,613 | A | | 8/1989 | Fry et al. |
| 4,938,216 | A | * | 7/1990 | Lele .............................. 601/3 |
| 4,955,365 | A | | 9/1990 | Fry et al. |
| 5,036,855 | A | | 8/1991 | Fry et al. |

(Continued)

FOREIGN PATENT DOCUMENTS

DE 19746321 4/1999

(Continued)

OTHER PUBLICATIONS

WO8907909.*

(Continued)

*Primary Examiner*—Brian Casler
*Assistant Examiner*—Parikha S Mehta
(74) *Attorney, Agent, or Firm*—Husch Blackwell Sanders Welsh & Katz

(57) ABSTRACT

The invention relates to a treatment probe for focused ultrasound including a probe body, which is mounted in rotation around an axis; an elongated treatment transducer with a focused ultrasound emission acoustic axis, which is more or less the same as the rotation axis of the probe body; and an imaging transducer, the imaging plane of which contains the acoustic axis of the treatment transducer. The inventive probe can be used to provide a simple treatment. The probe body can be rotated around the axis in order to vary the direction of the imaging plane without moving the focus, which always remains in the imaging plane. The treatment transducer can be extended in order to provide safer treatment in relation to the organs to be treated and without risk of damaging the fragile surrounding organs.

25 Claims, 7 Drawing Sheets

U.S. PATENT DOCUMENTS

| | | | |
|---|---|---|---|
| 5,078,124 A * | 1/1992 | Viebach et al. | 601/4 |
| 5,095,907 A * | 3/1992 | Kudo et al. | 600/439 |
| 5,178,135 A * | 1/1993 | Uchiyama et al. | 601/4 |
| 5,273,027 A * | 12/1993 | Sekino et al. | 601/54 |
| 5,391,140 A | 2/1995 | Schaetzle et al. | |
| 5,431,621 A | 7/1995 | Dory | |
| 5,448,994 A * | 9/1995 | Iinuma | 600/439 |
| 5,727,556 A | 3/1998 | Weth et al. | |
| 5,938,612 A * | 8/1999 | Kline-Schoder et al. | 600/459 |
| 6,007,499 A * | 12/1999 | Martin et al. | 601/3 |
| 6,036,661 A * | 3/2000 | Schwarze et al. | 601/4 |
| 6,068,596 A | 5/2000 | Weth et al. | |
| 6,071,238 A | 6/2000 | Chapelon et al. | |
| 6,328,697 B1 * | 12/2001 | Fraser | 600/459 |

FOREIGN PATENT DOCUMENTS

| | | |
|---|---|---|
| EP | 0148 653 | 9/1987 |
| EP | 0162 735 | 11/1990 |
| EP | 0273 180 | 6/1991 |
| EP | 0273 180 B1 | 6/1991 |
| EP | 0714 266 | 10/1998 |
| EP | 0714 266 B1 | 10/1998 |
| JP | 09-276274 | 10/1997 |
| JP | 10-216145 | 8/1998 |
| JP | 2003-513643 | 4/2003 |
| WO | WO 89/07909 | 9/1989 |
| WO | WO 92/15253 | 9/1992 |
| WO | WO 95/02994 | 2/1995 |
| WO | WO 03/008041 | 1/2003 |

OTHER PUBLICATIONS

PCT/FR/02/02367*

* cited by examiner

FIG_1
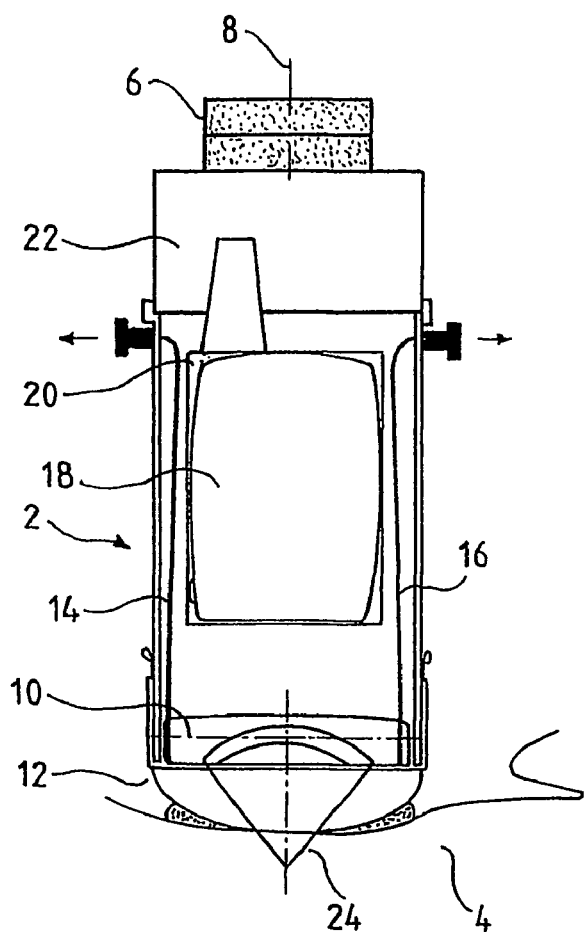
FIG_2
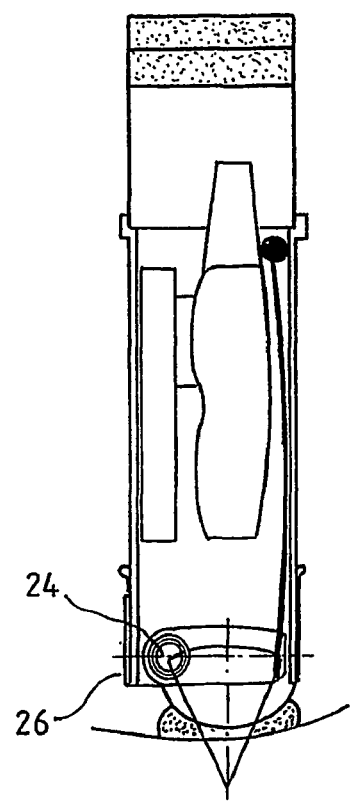
FIG_3
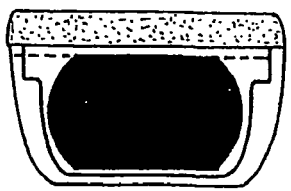

FIG_4
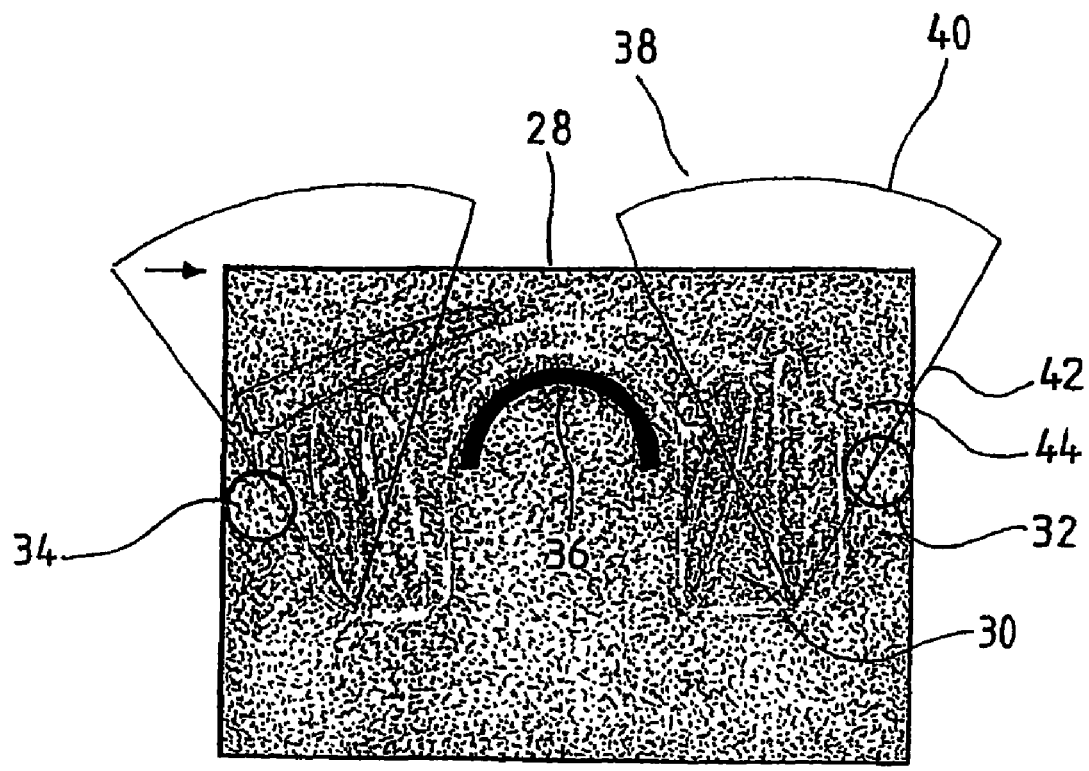

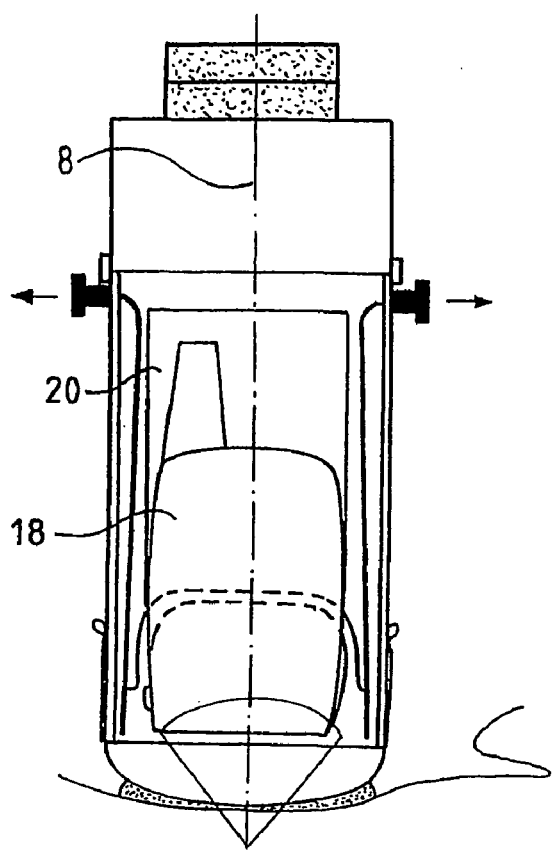
FIG_5
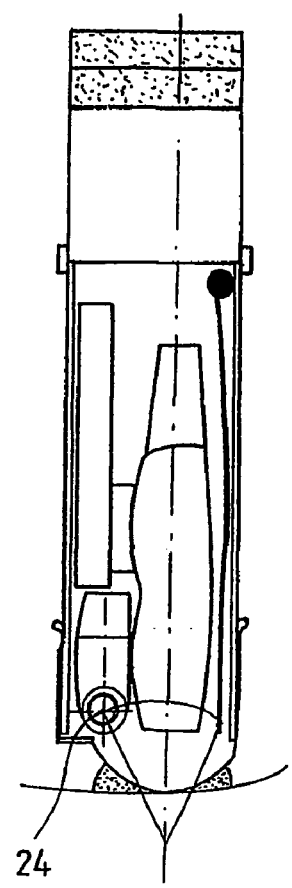
FIG_6
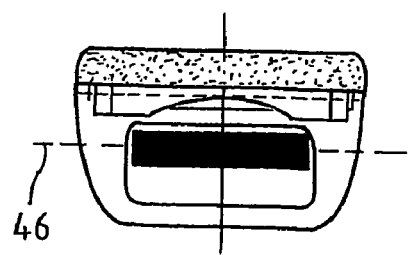
FIG_7

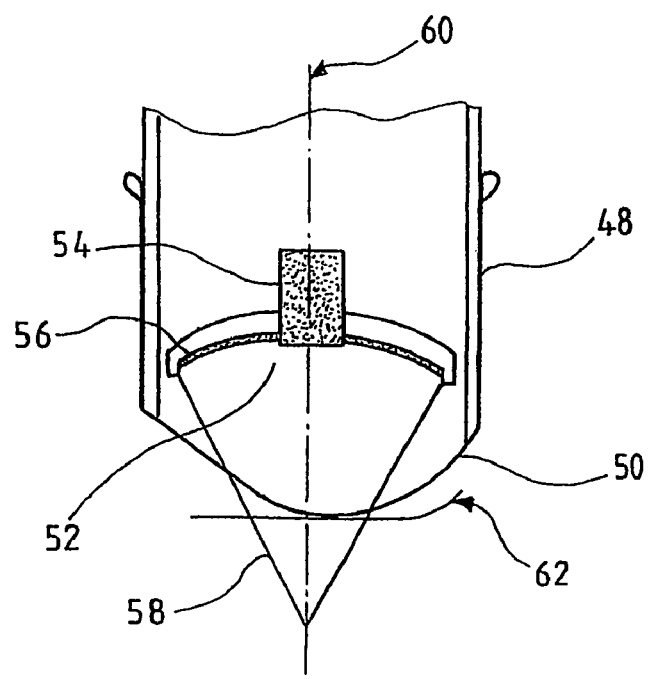
FIG_8
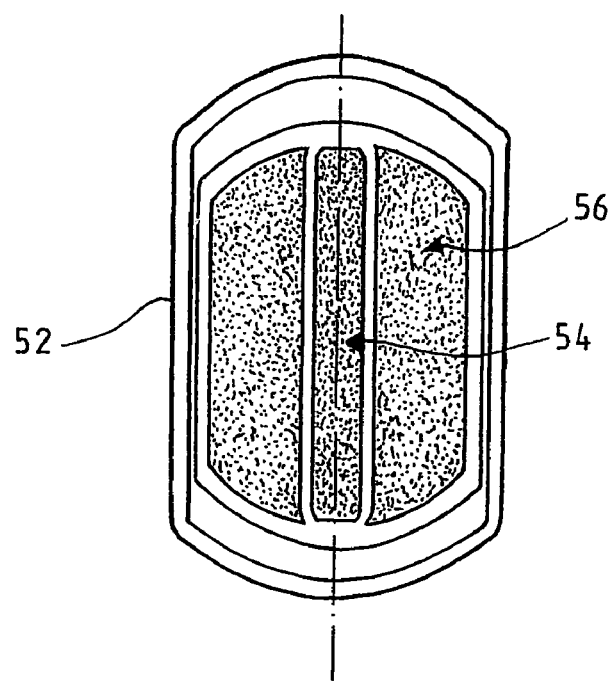
FIG_9

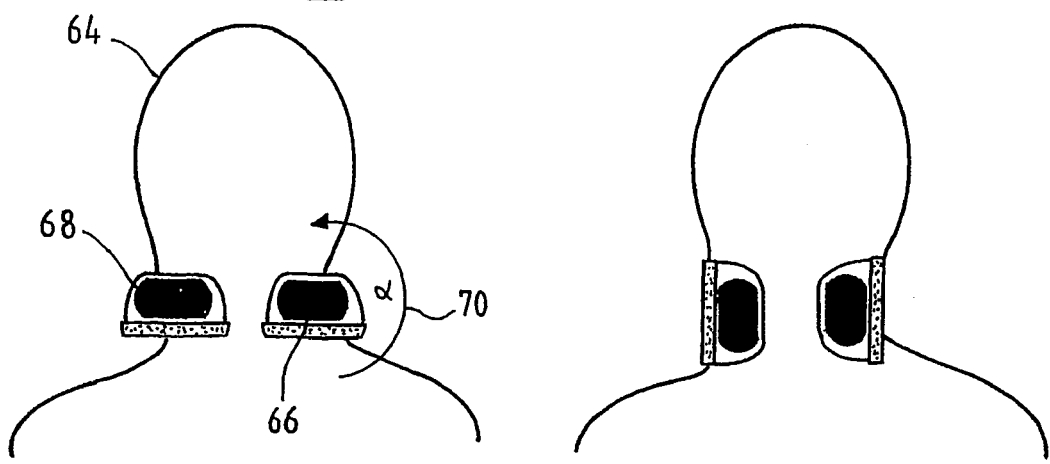
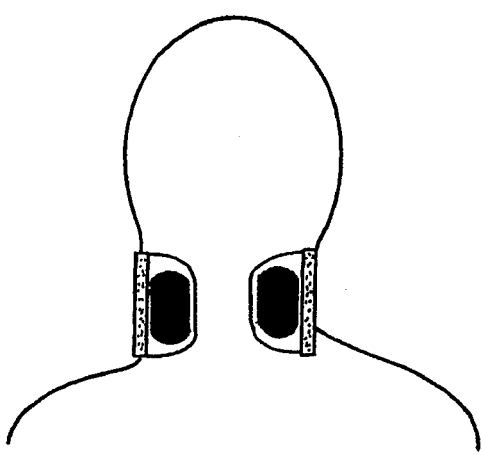
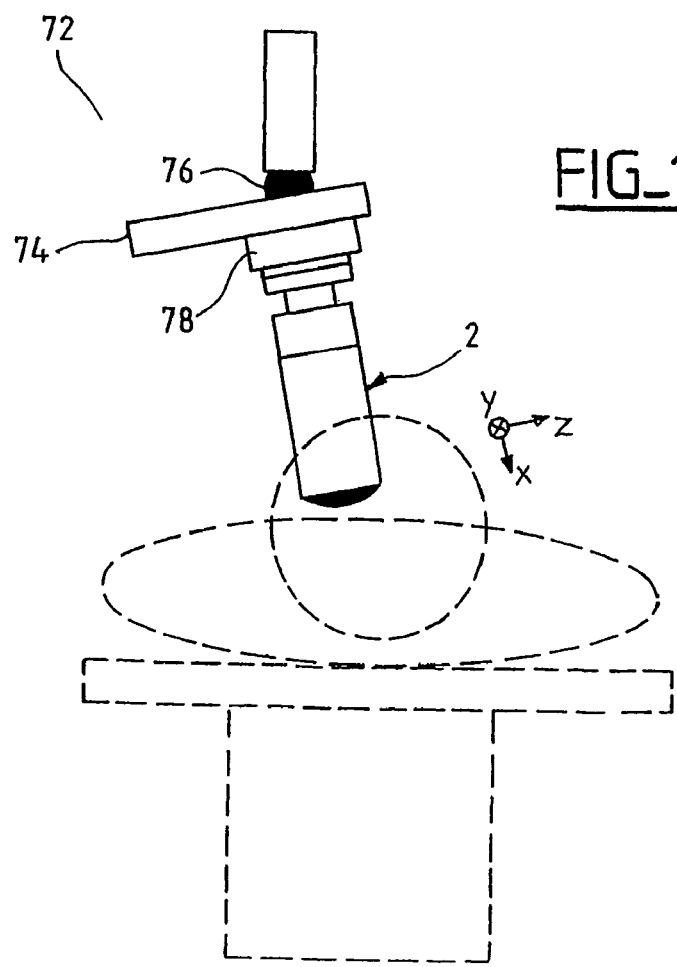

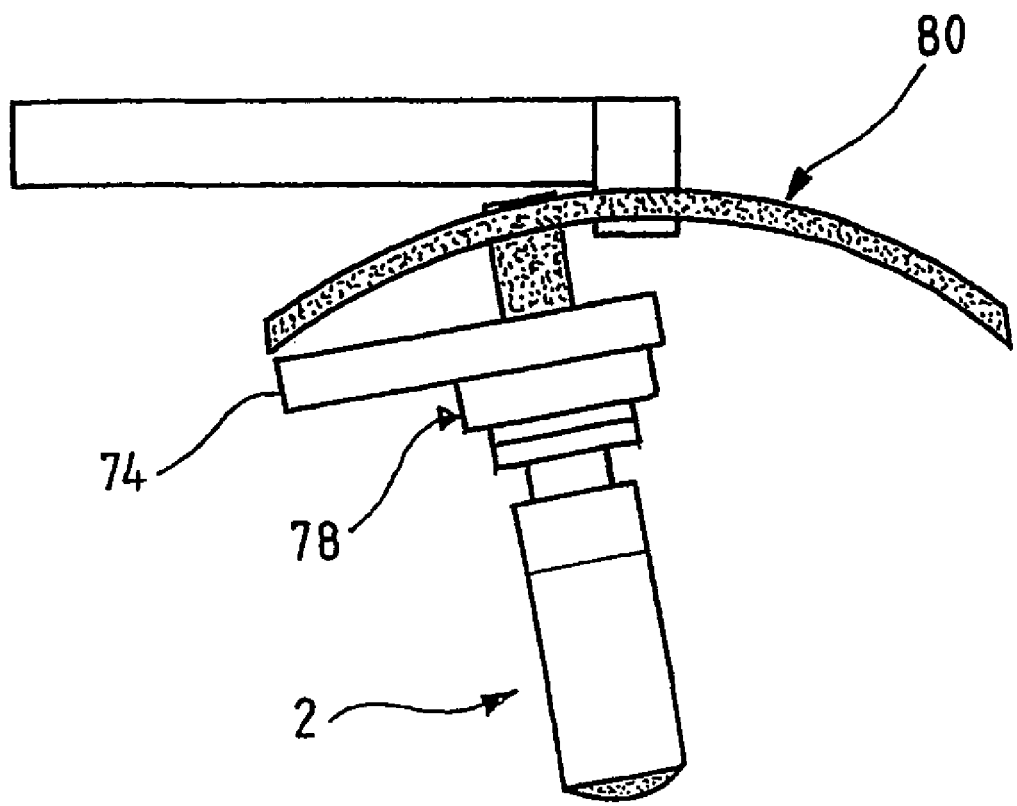

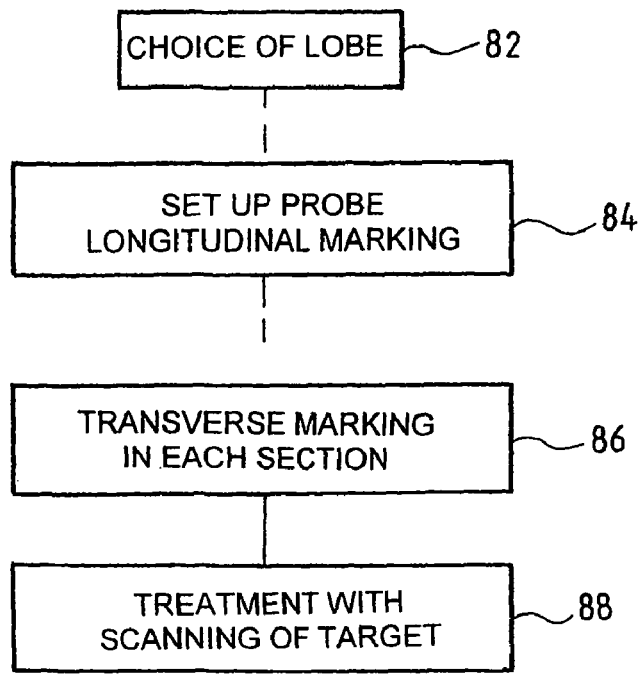
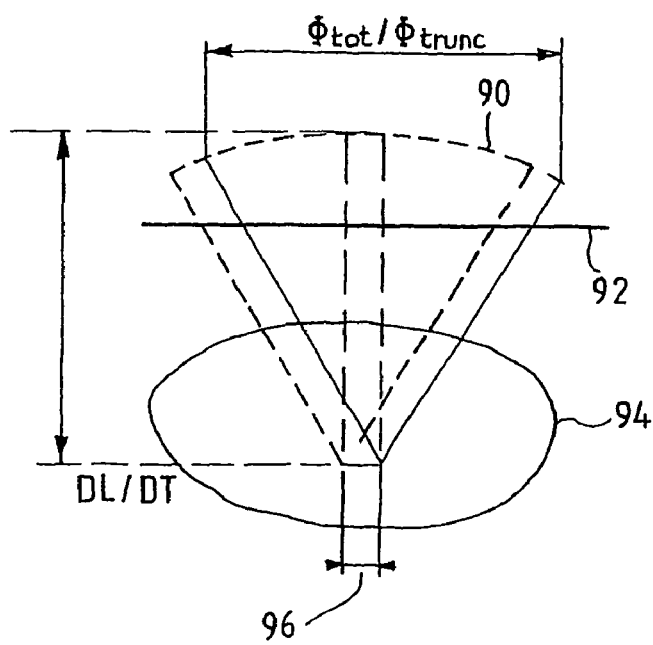

ULTRASONIC IMAGING AND TREATMENT PROBE HAVING AN ASYMMETRIC FOCAL ZONE

FIELD OF THE INVENTION

The present invention relates to the field of focused ultrasound, and more precisely, to treatment by focused ultrasound.

BACKGROUND OF THE INVENTION

Focused ultrasound makes it possible to treat deep tissues without direct access to these tissues. A focused ultrasound beam originating from a power transducer is concentrated towards a focus which is positioned on the target. This results in a double thermal and cavitation phenomenon. The tissue effect depends on the application of the ultrasound energy. Under certain conditions (moderate acoustic intensity), a thermal effect is obtained, under others (strong acoustic intensity), the cavitation effect predominates. The choice of treatment parameters (acoustic intensity and frequency, duration of firing, duration of pauses between the firings, spacing between the firings etc.) is made in order to avoid burning in the intermediate tissues, i.e., situated between the ultrasound source and the target. The designation "acoustic axis" of the transducer is given to a line joining the center of the transducer, or its center of symmetry (if it exists) and the focus. In the case of a plane transducer and electronic focusing, the acoustic axis is the axis perpendicular to the transducer plane, and passing through the focus; the acoustic axis can also generally be defined as passing through the focus and directed following the mean direction of ultrasound propagation.

The effect of each ultrasound pulse is generally limited to a small spatial zone, in which the intensity of the ultrasound field is strongest, and which is situated around the focus. The focal zone will typically have the shape of a cylinder 1.5 mm in diameter in a plane perpendicular to the acoustic propagation direction and 10 mm in length in the acoustic propagation direction.

This technique is particularly useful when the treatment must be precise, for example when the zone to be treated is close to sensitive organs to be preserved. This is the case for example with treatment of the prostate, in which the external sphincter must not be touched for fear of causing incontinence in the patient.

It has therefore been proposed to combine in one therapy appliance a treatment transducer and an imaging transducer; in fact ultrasound marking is useful because it is simple, inexpensive and emits no ionizing radiation. The imaging transducer is used, as its name indicates, to obtain an image of the zone to be treated. The treatment transducer, or power transducer, is used for the emission of the ultrasound intended for the treatment. From the quantitative point of view, the average power range for the imaging transducer is typically of the order of 0.1 to 1 W, while the average power range for the treatment transducer is typically of the order of 5 to 100 W. Moreover, the ultrasound pulses emitted for the imaging have a typical duration of 0.1 µs to 1 µs, whilst the therapy pulses last from 0.1 s to 20 s. In order to make it possible to visualize a volume containing the target, a displacement of the imaging transducer scanning plane can be provided.

Ultrasound therapy appliances combined with ultrasound scanning have been described. In EP-A-0 148 653, EP-A-0 162 735 and U.S. Pat. No. 5,431,621, an imaging transducer is accommodated in the center of a cap serving as treatment transducer; this cap has axial symmetry. The scanning plane of the imaging transducer contains the acoustic axis of the treatment transducer. The ultrasound imaging transducer can turn on its axis, but this is not the case with the treatment transducer. It is proposed in these documents to use the appliance to destroy renal calculi by shock waves or to treat tumors by hyperthermia.

WO-A-92 15253 describes a bevelled endorectal probe. The probe is mounted in rotation on a support and in translation along its longitudinal axis. The treatment transducer is fixed with respect to the probe body. The probe has an imaging transducer, which is fixed or mobile with respect to the treatment transducer. In all cases, the imaging transducer's scanning plane contains the focus of the treatment transducer.

EP-A-0-714 266 describes an endorectal probe suitable for treatment of the prostate. The probe comprises retractable therapy and imaging transducers. In the "imaging" position, the second transducer scans a plane containing the acoustic axis of treatment. The scanning plane is variable, as it can pivot about this axis. The treatment transducer does not turn about its acoustic axis, but about an axis which is parallel to the axis of the endorectal probe.

WO-A-89 07909 discloses, in FIG. 2, an extracorporeal treatment appliance comprising an imaging transducer and a treatment transducer. Each of the transducers is mounted at the end of a tube; the two tubes are mounted on a disk and extend perpendicularly to the plane of the disk. The disk is mounted in rotation in the appliance. The tube carrying the treatment transducer is approximately in the center of the disk; this tube is mobile in translation along its axis. At the end of the tube, the treatment transducer is mounted in rotation on an axis perpendicular to the axis of the tube. The treatment transducer thus has three degrees of freedom, in order to be oriented in all directions. The imaging transducer is mounted in analogous fashion; in all cases, the scanning plane of the imaging transducer contains the focus of the treatment transducer. The axis of rotation of the disk—which is the longitudinal axis of the tube carrying the treatment transducer—generally corresponds neither to the acoustic axis of the treatment transducer, nor to that of the imaging transducer; in fact, for a given treatment depth, the scanning movement of the target through the focal point is carried out by rotation of the treatment transducer about the axis perpendicular to the tube.

WO-A-95 02994 discloses, in FIG. 5, a probe suitable for visualizing and treating tissues situated in the probe's longitudinal axis, such as liver tumors or fibromas. This probe has an imaging transducer and a therapy transducer mounted back to back, the whole assembly being mounted in rotation at the end of the probe, about an axis perpendicular to the axis of the probe. The rotation of the probe body makes it possible to modify the scanning plane of the probe. The rotation of the transducers ensures scanning or treatment in the plane concerned. As in the preceding document, the axis of rotation of the probe body—which is the longitudinal axis of the probe—does not generally correspond to the acoustic axis of the treatment transducer. EP-A-0 273 180 discloses a probe of the same type.

These different appliances of the state of the art are only slightly or not at all suitable for the treatment of organs from outside the body, and for example for focused ultrasound treatment of the thyroid. A need therefore exists for an appliance which can treat organs such as the thyroid, by focused ultrasound, simply, with precision, and effectively.

SUMMARY OF THE INVENTION

In one embodiment, the invention provides a focused ultrasound treatment probe, which is suitable for treatment of different organs from outside the body. The probe has a probe body which is mounted in rotation on a support. The probe body comprises an elongated treatment transducer, the acoustic axis of which is substantially the same as the axis of rotation of the probe body. The probe body also has an imaging transducer, the scanning plane of which contains the acoustic axis of the treatment transducer.

The fact that the transducer is elongated allows high-precision emission: the cone formed by the acoustic waves is asymmetrical and has an angle at the apex—at the focus—which is less open in the transverse direction of the transducer than in the longitudinal direction of the transducer. It is easier to avoid the organs close to the target. The fact that the acoustic axis is substantially the same as the axis of rotation of the probe body ensures that the probe body can turn about the axis of rotation, without however the position of the focus with respect to the target moving. It is then possible to displace the probe body in rotation, for imaging or treatment, without however displacing the transducers.

As the scanning plane—or imaging plane—of the imaging transducer contains the acoustic axis and therefore also contains the axis of rotation of the probe body, the target being situated at the focus of the treatment transducer remains in the imaging plane during rotation of the probe body.

The invention moreover proposes that the treatment transducer be mounted so that it is mobile in the probe body. It is in particular possible for the treatment transducer to be mounted in rotation in the probe body about an axis perpendicular to the axis of rotation.

This configuration makes it possible for the imaging transducer to also be mounted so that it is mobile in the probe body. It can in particular be mounted in translation in the probe body, preferably following a direction parallel to the axis of rotation.

In one embodiment, the treatment transducer has an aspect ratio greater than 1.2. It is also advantageous for the treatment transducer to have an aspect ratio smaller than 2.5.

Preferably, the imaging transducer is an array carrying out a linear scan. It is then advantageous for the axis of this transducer to be parallel to the longitudinal direction of the treatment transducer. The imaging transducer can in particular be integrated into the treatment transducer.

In another embodiment, the probe has a support on which the probe is mounted in rotation, the support displacing the probe in translation in a plane perpendicular to the axis of rotation. In this case, the support can moreover displace the probe in translation following the direction of the axis of rotation.

The support can also have a ball-and-socket joint for orientation of the probe. Another solution is for the support to have an arch along which the probe moves; it is then advantageous for the radius of the arch to be substantially equal to the distance between the arch and the focus of the treatment transducer.

A subject of the invention is therefore a focused ultrasound treatment probe, comprising a probe body mounted in rotation about an axis, an elongated treatment transducer, with an acoustic axis of focused ultrasound emission substantially the same as the axis of rotation of the probe body, an imaging transducer the imaging plane of which contains the acoustic axis of the treatment transducer.

According to one embodiment, the treatment transducer is mounted so that it is mobile in the probe body.

According to another embodiment, the treatment transducer is mounted in rotation in the probe body preferably about an axis perpendicular to the axis of rotation.

According to yet another embodiment, the imaging transducer is mounted so that it is mobile in the probe body.

According to yet another embodiment, the imaging transducer is mounted in translation in the probe body, preferably following a direction parallel to the axis of rotation.

It can also be provided that the treatment transducer has an aspect ratio greater than 2.2. It can advantageously be provided that the treatment transducer has an aspect ratio smaller than 2.5.

According to one embodiment, the imaging transducer is an array carrying out a linear scan.

According to another embodiment, the imaging transducer axis is parallel to the longitudinal direction of the treatment transducer.

According to yet another embodiment, the imaging transducer is integrated in the treatment transducer.

According to yet another embodiment, the probe has a support on which the probe is mounted in rotation, the support displacing the probe in translation in a plane perpendicular to the axis of rotation.

It can moreover be provided that the support moreover displaces the probe in translation following the direction of the axis of rotation.

According to one embodiment, the support has a ball-and-socket joint for orientation of the probe.

According to yet another embodiment, the support has an arch along which the probe moves.

According to another embodiment, the radius of the arch is substantially equal to the distance between the arch and the focus of the treatment transducer.

Other characteristics and advantages of the invention will become apparent on reading the following description of embodiments of the invention, given by way of example and with reference to the attached drawings.

BRIEF DESCRIPTION OF THE DRAWINGS

FIG. 1 is a diagrammatic view in longitudinal section of a probe, following the longitudinal direction of the treatment transducer;

FIG. 2 is a diagrammatic view in longitudinal section of the probe of FIG. 1, following the transverse direction of the treatment transducer;

FIG. 3 is a diagrammatic view of the face of the probe of FIGS. 1 and 2;

FIG. 4 is a diagrammatic view of the probe of FIGS. 1 and 2, being used for treatment of the thyroid;

FIGS. 5, 6 and 7 are diagrammatic views corresponding to FIGS. 1, 2 and 3, when the probe is in the imaging position;

FIG. 8 is a partial diagrammatic view of another example of a probe, in longitudinal section following the longitudinal direction of the treatment transducer;

FIG. 9 is a partial diagrammatic view of the face of a probe of FIG. 8;

FIGS. 10 and 11 are views of the position of the probe body with respect to a patient, being used for treatment of the thyroid;

FIG. 12 is a diagrammatic view of an example of a probe, showing the probe support;

FIG. 13 is a view analogous to that of FIG. 12, for another example of a probe support;

FIG. 14 is a flowchart showing treatment using a probe; and

FIG. 15 is a view of the treatment transducer explaining the firing parameters.

DETAILED DESCRIPTION

In this written description, the use of the disjunctive is intended to include the conjunctive. The use of definite or indefinite articles is not intended to indicate cardinality. In particular, a reference to "the" object or thing or "an" object or "a" thing is intended to also describe a plurality of such objects or things.

FIGS. 1 to 7 show an example in which the treatment transducer and the imaging transducer are mobile in the probe body; in contrast, FIGS. 8 and 9 show an example in which the treatment transducer and the imaging transducer are fixed in the probe body.

FIG. 1 is a diagrammatic view in longitudinal section of a probe, following the longitudinal direction of the treatment transducer. The longitudinal section of the probe is made in a plane containing the axis of rotation of the probe body; it can be seen in the example in FIG. 1 that the probe body is elongated in shape and that the longitudinal axis of the probe body is the same as that of the axis of rotation. The longitudinal direction of the transducer is defined, due to the elongated shape of the treatment transducer, as the direction following which the treatment transducer has the largest dimension; the transverse direction of the treatment transducer, in contrast, is the direction perpendicular to the acoustic axis following which the dimension of the treatment transducer is the smallest.

FIG. 1 shows the probe body 2, as well as a part of the patient 4 during treatment. The probe body is mounted in rotation on a probe support (not represented), by a connection 6; the axis 8 is the axis of rotation of the probe body on the probe support. In its frontal part, which is directed towards the zone of the patient to be treated, the probe body has the treatment transducer 10. The example in the figure is a bevelled transducer, as shown in FIG. 3. The treatment transducer has in the example a natural focusing, due to its shape; it could also be formed from a plurality of transducers which can be excited independently, and have electronic focusing. The end of the probe body is formed by a small balloon 12, which is flexible and transparent to ultrasound. This balloon is inflated by a coupling fluid which is transparent to ultrasound, using fluid conduits 14 and 16. The conduits are fixed on the probe body in order to allow easy cleaning, or can be easily changed; these conduits are terminated by connectors for the injection, extraction or circulation of the coupling fluid; these conduits advantageously emerge in the vicinity of the balloon. The coupling fluid described in FR 99 03738 can be used, which is cooled down in order to protect the treatment transducer against overheating and to protect the surface of the skin against burning; the fact that the conduits emerge in the vicinity of the balloon makes it possible to preferentially cool down the balloon in the vicinity of the skin. The level of the fluid in the probe body is chosen—in the example in FIGS. 1 to 3—such that the height of the fluid and therefore the pressure in the balloon are constant when passing from the imaging mode to the treatment mode. This constraint does not exist in the example in FIGS. 8 and 9.

Moreover, a mask is provided, the function of which is explained with reference to FIG. 2. The figure also shows the imaging transducer 18, as well as the plate 20 on which this transducer is mounted in translation following the longitudinal axis of the probe. The imaging transducer is, for example, an ultrasound linear rod, which ensures high-precision imaging. The rear part 22 of the probe body, opposite the frontal part, contains the transducer displacement actuators.

FIG. 1 also shows the behavior of the ultrasound beam, which, in the plane of the longitudinal direction of the treatment transducer, is conical in shape; the apex of the cone 24 is the focus, on which the ultrasound is concentrated. In treatment, the apex covers the target.

As shown in the figure, the axis of rotation 8 of the probe body passes substantially through the focus, the treatment transducer extends in a plane which is substantially perpendicular to the axis of rotation 8; thus the acoustic axis of the transducer is substantially the same as the axis of rotation of the probe. In practice, it is advantageous for the acoustic axis to be exactly the same as the axis of rotation of the probe—allowing for any mechanical clearances. Nevertheless a displacement can be allowed between the acoustic axis and the axis of rotation, to the extent that the displacement of the focal point during the rotation of the probe body about the axis of rotation remains limited, and typically remains smaller than the transverse dimension of the focal zone. In terms of distance, the distance between the acoustic axis and the probe axis is advantageously less than 1 mm, throughout the zone extending between the focus and the treatment transducer; in terms of angles, an angle can be allowed between the direction of the acoustic axis and the direction of the axis of rotation of up to 15°.

FIG. 2 is a diagrammatic view in longitudinal section of a probe, following the transverse direction of the treatment transducer. The figure shows the elements already described with reference to FIG. 1. FIG. 2 also shows that the treatment transducer is mounted in rotation about a shaft 24; the rotation of the treatment transducer allows it to be retracted in order to allow the imaging transducer to pass when the probe is in the imaging position, as represented in FIGS. 5, 6 and 7. FIG. 2 also shows the function of the mask; due to the presence of the plate 20 and the shaft 24, the probe body is not symmetrical with respect to the plane containing the axis of rotation and the longitudinal direction of the treatment transducer. The balloon surrounds the end of the probe body; the mask 26 has the function of limiting the deformations of the balloon in the vicinity of the shaft 24. Thus, the balloon rests on a rigid contour, defined by the edges of the probe body and by the mask; this contour is symmetrical or substantially symmetrical with respect to the axis of rotation or with respect to the acoustic axis 8 of the probe. The inflated balloon then has a shape which is symmetrical with respect to the acoustic axis; in particular, as the figures show, the foremost point of the balloon is substantially on the acoustic axis. This favors the positioning of the probe body with respect to the patient. When the probe body is moved in rotation about the axis 8, this ensures that the point of contact or the zone of contact between the balloon and the patient is also substantially on the axis of rotation.

FIG. 2 shows, like FIG. 1, the behavior of the ultrasound beam, which, in the plane of the transverse direction of the treatment transducer, is also conical in shape; the cone of FIG. 2 however has an angle at the center which is smaller than the angle at the center of the cone of FIG. 1. The difference in angle is representative of the aspect ratio of the treatment transducer, in other words the ratio between its longitudinal dimension and its transverse dimension. In the example, the transducer has a longitudinal dimension of the order of 54 mm, and a transverse dimension of the order of 35 mm. The ratio between these two dimensions, the aspect ratio of the treatment transducer—is 1.6. In practice, aspect ratio values comprised between 2.5 and 1.2 are suitable. The lower limit is determined by the desire to have a preferential direction for treatment; the upper limit is a function of the limitations on the size of the transducers and the ability of the ultrasound to pass through the tissues. The focal length of the transducer depends on the use envisaged and the depth of the organ to be treated. In the case of the thyroid, a focal length between 30 and 45 mm is suitable.

FIG. 2 also shows that the axis of rotation 8 of the probe body passes substantially through the focus of the treatment transducer. As explained above, with respect to the acoustic axis, it is advantageous for the axis of rotation to be exactly contained within the imaging plane; variations are possible, within the same ranges as those which are indicated above for the acoustic axis.

FIG. 3 is a diagrammatic front view of the probe body of FIGS. 1 and 2. It shows the treatment transducer, the mask, as well as the axis of the shaft 24. FIG. 3 clearly shows that the contour on which the balloon rests is substantially symmetrical with respect to the axis of rotation. The figure also shows that the treatment transducer is a bevelled transducer.

FIG. 4 is a diagrammatic view of the probe of FIGS. 1 and 2, being used for treatment of the thyroid; the figure represents a cross-section in a horizontal plane; it shows the skin 28 of the patient's neck, the thyroid 30, the two carotid arteries 32 and 34, as well as the trachea 36. The thyroid has two lobes which extend on either side of the trachea, and are practically in contact with the carotid arteries. The figure also shows the position of the ultrasound cone for the treatment of the right lobe of the carotid; it represents the ultrasound cone 38 or 40 for two positions of the probe; the focal zones 42 or 44 are also represented for these two positions of the probe. The figure shows that the gland is not very deep and therefore easily accessible to the ultrasound. However, in the transverse planes (with reference to the patient) the acoustic window between the trachea and the external part of the neck is relatively narrow. The elongated shape of the transducer, and the use of the transducer with the longitudinal direction parallel to the neck of the patient makes it possible to have, in the transverse direction, a cone more closed than in the longitudinal direction. This makes it possible to keep effective treatment—a given treatment transducer surface—whilst preserving the organs adjacent to the gland to be treated.

The figure does not show the recurrent laryngeal nerves which control the vocal chords and pass behind the two lobes of the thyroid gland. These nerves are protected during treatment, to the extent that they are situated behind the zone aimed at. The esophagus, which is situated behind the trachea, is also not shown.

In order to reinforce the safety of the treatment, it is also possible to use the probe described with a tracheal probe, which is installed in the patient's trachea during treatments. For example the probe can be an NIM Response® nerve integrity monitor, marketed by the company Xomed. It comprises electrodes placed in proximity to the recurrent laryngeal nerves, which thus make it possible to detect any alterations to these nerves due to the ultrasound energy emitted during the treatment.

It is also possible to use a tracheal probe comprising a balloon, positioned facing the thyroid and through which cold water circulates, which makes it possible to cool the trachea down and thus to protect it from any thermal damage. A probe combining electrodes and a cold circulation can also be used.

FIGS. 5, 6 and 7 are diagrammatic views corresponding to FIGS. 1, 2 and 3, when the probe is in the imaging position. In this position, the treatment transducer has tilted about the shaft 24 in order to become flattened against the probe body; on the other hand, the plate 20 moves the imaging transducer 18 forward, so that the latter occupies the place vacated by the treatment transducer. In this imaging position, the imaging plane—or scanning plane of the imaging transducer—contains the axis of rotation 8 of the probe body. Preferably, the emission surface of the imaging transducer is also perpendicular to the axis of rotation 8 of the probe body. This plane is parallel to the plane of FIG. 5 and is referenced 46 in FIG. 7. The presence of the plate makes it possible to move the imaging transducer towards or away from the tissue, in order to optimize the quality of the image. In fact, in certain cases, parasitic echoes are superimposed on the focal zone and the translation of the probe makes it possible to displace them. Moreover, certain ultrasonographs have a fixed focal length, and the displacement of the imaging transducer makes it possible to situate the target within the range in which the image is finest.

In the probe's imaging position, the imaging plane contains the acoustic axis, and therefore also contains the axis of rotation of the probe body. It is therefore possible, during the rotation of the probe body, to obtain in a continuous fashion, the image of the zone of the organ to be treated which is covered by the target. It is also possible to mark on the ultrasonographic image the position of the focus or even the position or extent of the lesions which will be made by the treatment transducer.

In order to return to the treatment position represented in FIGS. 1 to 3, the imaging transducer is withdrawn towards the rear of the probe body, and the treatment transducer is pulled down into place, in such a way that its acoustic axis is again the same as the axis of rotation of the probe body. Retraction of the imaging transducer during treatment makes it possible to have a maximum emission surface for the treatment transducer.

FIGS. 8 and 9 are partial diagrammatic views of another example of a probe, in longitudinal section following the longitudinal direction of the treatment transducer and in front view. The example of FIGS. 8 and 9 differs from the example of the previous figures in that the imaging transducer is integrated into the treatment transducer; in the example, the imaging transducer is placed in an aperture made in the treatment transducer. This makes any displacement of the imaging transducer or the treatment transducer unnecessary; consequently, the treatment transducer and imaging transducer can be in a fixed position inside the probe body. The latter can be symmetrical in shape with respect to the axis of rotation, and therefore, the mask is not necessary.

FIG. 8 therefore shows the wall 48 of the probe body, the balloon 50 arranged at its front end, the transducer 52 with the part 54 serving for the imaging and the part 56 serving for the treatment. As previously, the cone 58 formed by the ultrasound, the axis of rotation 60 and the patient's skin 62 have been included in the figures. As in the previous example, the treatment transducer is elongated in shape and its acoustic axis is substantially the same as the axis of rotation of the probe body.

FIGS. 10 and 11 are views of the position of the probe body with respect to a patient, being used in treatment of the thyroid; they show diagrammatically the patient 64, as well as a probe 66 or 68, in position in the vicinity of the left lobe or the right lobe of the thyroid. For the patient, the longitudinal direction is the direction going from the patient's head to feet, and the transverse direction is the direction going from one lobe of the thyroid to the other lobe.

FIG. 10 shows an imaging position of the probe body. In this position, the patient is recumbent and the probe is brought into contact with the skin of the patient's neck, facing the lobe concerned of the thyroid. The axis of rotation of the probe is then in a vertical plane, perpendicular to the transverse direction of the patient. As symbolized by the arrow 70 in FIG. 10, it is possible to move the probe body in rotation, about the axis of rotation, this makes it possible to vary the imaging plane of the imaging transducer.

FIG. 11 shows a treatment position of the probe body. In this position, the longitudinal axis of the treatment transducer is parallel to the patient's longitudinal axis. The elongated shape of the treatment transducer allows more precise treatment, without the risk of damaging the organs adjacent to the thyroid lobes.

FIG. 12 is a diagrammatic view of an example of a probe, showing the support of the probe body; this comprises a bracket 72, on which a translation plate 74 is mounted, by means of a ball-and-socket joint 76. A second translation plate 78 is mounted on the first plate, with a displacement direction perpendicular to that of the first plate. The probe body is mounted in rotation on the second plate 78, with a axis of rotation perpendicular to the displacement directions of the two plates. The directions x, y and z of the axis of rotation, the displacement direction of the second plate and the displacement direction of the first plate thus form an orthonormal marker.

FIG. 13 is a view analogous to that in FIG. 12, for another example of a probe support; the probe support in FIG. 13 differs from that in FIG. 12 in that the first plate 74 is mounted on the bracket by means of an arch 80, along which the first plate can move. The arch 80 is itself mounted in rotation on the bracket according to a vertical axis, which makes it possible to incline the probe in all directions. It is advantageous for the radius of the arch to be such that the displacement of the first plate 74 along the arch takes place about the focus. In other words, the radius of the arch is substantially equal to the distance between the arch and the focus.

In either case, the two plates allow displacement of the probe, perpendicularly to the acoustic axis. In fact, each acoustic pulse causes necrosis of the tissue in a small volume. In order to treat a complete target, the head is thus displaced between the firings, by means of the plates.

It is also advantageous to orient the front part of the probe substantially perpendicular to the skin. This makes it possible to keep a constant depth from one displacement of the head to another. The orientation is possible by means of the ball-and-socket joint in FIG. 12 or the arch in FIG. 13. Both ensure a constant depth.

The probe described has the following advantages. First it ensures precise marking. In fact, the treatment transducer is combined with an imaging transducer, procuring a very fine image and capable of visualizing the whole target. To the extent that the relative positions of the treatment transducer and of the imaging transducer can be determined precisely—in both examples—the images obtained by means of the imaging transducer are in a known and precise spatial relationship with the focal zone of the treatment transducer; the effect of the ultrasound is produced well in the zone visualized by the imaging transducer. The rotation of the probe body about an axis which is the same as the acoustic axis of the treatment transducer and which is contained in the imaging plane ensures high precision, even during displacements of the probe.

The probe also ensures safe treatment, in particular in the case of treatments of the thyroid. The recurrent laryngeal nerves are protected by the two lobes of the thyroid gland. The depth positioning of the focal point, by appropriate inflation of the balloon, ensures high precision depth treatment. The trachea is protected by the positioning of the probe body. The esophagus is situated behind the trachea and protected by the latter. The high volume of blood flow in the carotid protects it from the thermal effects of the ultrasound. As explained above, the elongated shape of the treatment transducer makes it possible to preserve the tissues, by using an ultrasound beam in the form of a flattened cone.

The probe also ensures effective treatment. In order to obtain a treatment effect, for example by coagulation of the tissue in the focal zone, the ultrasound waves must be sufficiently concentrated. For this purpose, the diameter of the transducer is generally allowed to be equal to its focal length. Moreover, the power is a function of the emissive surface. The elongated shape of the transducer makes it possible to satisfy the requirement relating to the diameter of the transducer, without reducing the emissive surface.

The probe is also simple to use. In fact, it can easily be adapted to all patients—the contact area of the probe—the projection onto the patient following the acoustic axis, or the probe's contact zone with the patient is minimal, and corresponds substantially to the size of the therapy transducer.

An example of the probe's functioning sequence is now described, with reference to FIG. 14. Reference is made to a screen, which can indicate to the operator the instructions to be followed and allow him to visualize the images obtained by the imaging transducer, as well as the means of entering the target limits; these entry means can typically comprise a pointing device of any kind. The whole treatment is then computer-controlled; the use of a computer or similar equipment for controlling an ultrasound treatment appliance is known per se and is not explained in detail.

At step 82, the operator starts by indicating which side of the patient is treated—right or left. The longitudinal orientation of the probe depends on the side to be treated, as shown in FIG. 11. The probe is then switched to marking or imaging mode. This can consist of passing from the position in FIG. 1 to that in FIG. 5. Alternatively, in the case of the probe in FIG. 8, it is sufficient to switch the pulse generator of the imaging and treatment transducers.

At step 84, the probe is applied to the patient and oriented in the longitudinal axis of the patient. At this step, the transducer, its acoustic beam and the future lesion can be symbolized on the screen. The practitioner marks on the image the extreme positions "head" and "feet", which correspond to the cephalo-caudal extension of the target. This marking defines a series of "sections" or successive treatment planes, which are oriented transversally with respect to the patient. The practitioner also marks the position of the skin, for subsequent calculation of the power to be delivered during the firings. This step makes it possible to determine the successive positions of the probe, following the longitudinal direction of the patient. The distance between the "sections" is a function of the size of the zone surrounding the focus in which the tissues are treated. A distance between 10 and 30 mm is suitable.

At step 86, the probe is then displaced towards the first section, which is the position marked "head". The probe can then be oriented in the transverse axis of the patient. To this end, the transducer, its acoustic beam as it will be during treatment, i.e. when the probe is oriented longitudinally, and the future lesion are symbolized on the screen. The operator can mark the lesions to be treated in the first section.

The operator then displaces the probe towards the second section, in the caudal direction. He follows the same procedure as for the first section, marking the skin and lesions to be treated in this second section. The probe is then displaced towards the following sections, carrying out the marking each time.

At the end of these steps 82 to 86, the contours of the target are determined, and in each section the limits chosen by the operator for the ultrasound treatment are known. A different procedure can of course be followed, for example reversing the scanning directions and using "vertical sections". However the marking of the contours of the target on the horizontal sections makes it easier to avoid the structures to be preserved, such as the trachea, or the nerves, because these can easily be seen on the transverse sections through the neck. During steps 84 and 86, it is possible to turn the probe, in order to vary the direction of the imaging plane, as explained in detail above.

At step 88, the probe is then switched to firing mode; this can consist of passing from the position in FIG. 5 to that in FIG. 1. Alternatively, in the case of the probe in FIG. 8, it is sufficient to re-switch the transducers' pulse generator; the probe is positioned in rotation in such a manner that the longitudinal axis of the treatment transducer is the same as the patient's longitudinal axis. The treatment is then carried out, by scanning the target following the position parameters defined in steps 84 and 86. Indications relating to the treatment parameters are given below. Preferably, and because there is always a risk of the patient moving, the first firings take place in proximity to the structures to be preserved. In the case of treatment of the thyroid, it is preferable to treat the internal plane first, based on the supposition that the position of the patient at the start of a treatment sequence is correct, and that if it evolves, it only does so afterwards. In the vertical direction, it is preferable to treat the caudal sections first.

By way of example, possible treatment parameters are now given, in the case of the thyroid. FIG. 15 shows a view of the treatment transducer with the notations used. The figure includes a diagrammatic representation of the treatment transducer 90, the skin 92, and the target 94. The figure shows the focal length—the distance between the treatment transducer and the focus measured on the acoustic axis 96. It also shows the distance between the treatment transducer and the skin, also measured along the acoustic axis. The figure shows, in continuous lines, one position of the treatment transducer, and in broken lines, another position of the treatment transducer.

The following notations are used:

f excitation frequency of the transducer $P_{refE}$ reference power of the transducer in W: this is the electrical power to be supplied for the transducer to generate the intensity required at the focus in order to obtain coagulation necrosis of the tissues in the focal zone;

η electro-acoustic yield of the transducer: ratio between the acoustic power supplied by the transducer and the electric power used;

$P_{refA}$ reference power of the transducer in W: this is the electrical power which must be supplied by the transducer in order to obtain coagulation necrosis of the tissues in the focal zone; it is defined by $P_{refA}=P_{refE}*\eta$ $D_{foc}$ focal length of the transducer. Short focal lengths will be preferable for thin patients;

$\Phi_{tot}$ diameter of the transducer, or dimension of the transducer according to its longitudinal direction;

$\Phi_{trunc}$ truncated diameter of the transducer or dimension of the transducer according to its transverse direction;

The latter two parameters can be expressed as a function of "the aperture" which is the ratio between the large diameter and the focal length. $N=\Phi_{tot}/D_{foc}$ and the truncation parameter $R=\Phi_{trunc}/\Phi_{tot}$ which is the inverse of the aspect ratio discussed above.

It is also noted that:

$D_L$ spacing between the points in the longitudinal direction;

$D_T$ spacing between the points in the transverse direction;

$T_{on}$ duration of each pulse;

$T_{off}$ interval between each pulse.

The power can be calculated by compensating for the absorption of the tissues by an increase in the power according to the formula:

$$P=P_{ref}*\exp(2*\alpha*1*D_{ep}/10)$$

where:

α, absorption coefficient of the tissues in Np/cm/MHz. For HIFU treatments, a value (0.06 to 0.08) will be used which is higher than those given by various bibliographical sources, which can be used in ultrasonography (typically 0.04 to 0.05).

$D_{ep}$ thickness of the tissues crossed in mm $D_{ep}$ is a function of the distance to the skin and the focal length, $D_{ep}=D_{foc}-S$ with:

SDistance from the transducer to the skin.

It has been shown experimentally that the following parameters are particularly suitable for the treatment of thyroid nodules in humans. The minimum and maximum permitted values are designated minn and maxx, the recommended value range limits min and max, and Typ is a typical value considered by way of example.

| | | minn | Min | Typ | max | maxx | |
|---|---|---|---|---|---|---|---|
| Pref A | W | 5 | 9 | 11 | 13 | 18 | Reference power of the transducer |
| α | Np/cm/MHz | 0.05 | 0.06 | 0.07 | 0.08 | 0.1 | Absorption coefficient of the tissues |
| F | MHz | 2 | 2.5 | 3 | 3.5 | 4.5 | Excitation frequency of the transducer |
| Dfoc | mm | 25 | 30 | 40 | 45 | 50 | Focal length of the transducer |
| S | mm | 10 | 12 | 15 | 25 | 40 | Distance from the transducer to the skin |
| N | | 1.00 | 1.04 | 1.25 | 1.36 | 1.43 | Transducer aperture |
| R | | 51% | 61% | 70% | 76% | 100% | Transducer truncation |
| DL | mm | | 1.6% | 1.7% | 1.8% | | Spacing of points in the longitudinal direction |
| DT | mm | | 1.6% | 1.7% | 1.8% | | Spacing of points in the transverse direction |
| Ton | s | 2 | 2.5 | 3 | 3.5 | 6 | Duration of each pulse |
| Toff | s | 3 | 5 | 10 | 15 | 20 | Interval between each pulse |

These values allow treatment in one session of a unit/total duration of approximately 15 minutes. It is found, over a period of several weeks after the treatment, that the nodules disappear, the tissue treated being replaced by a fibrosis.

Of course, the present invention is not limited to the examples and embodiments described and represented, but it is capable of a number of variants accessible to a person skilled in the art. It would thus be possible to use other elongated shapes of treatment transducers. The kinematics of the imaging transducer and the treatment transducer can be different from that mentioned in FIGS. 1 to 7. Thus it would be possible to provide a third displacement for the probe, parallel to the acoustic axis, if the practitioner wishes to move the probe away from or towards the tissue. The ball-and-socket joint in FIG. 12 can be replaced by two perpendicular axes.

It is also clear that the probe is not limited to the preferred use of treatment of the thyroid; it can also be used for the treatment of other organs, such as for example tumors in the neck region, breast tumors, bone tumors or any other organ or tissue anomaly accessible to ultrasound by extracorporeal route. The firing parameters provided in the table can be modified, depending on the organ to be treated, the therapeutic effect sought, transducer characteristics etc.

Specific embodiments of a treatment probe for focused ultrasound according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. A treatment probe for coagulating a target by applying focused ultrasound at the target, comprising:
    a probe body mounted for rotation about a rotation axis, the probe body carrying a treatment transducer and an imaging transducer;
    wherein the treatment transducer coagulates the target by emitting focused ultrasound along an acoustic axis towards a focus, in which the focused ultrasound forms a cone having an apex, said apex being the focus and the cone having an angle at the apex which is less open in a first direction of the treatment transducer than in a second direction of the treatment transducer; and
    wherein the imaging transducer that is capable of obtaining an image of the target;
    wherein the treatment probe has a treatment mode in which the acoustic axis of the treatment transducer is substantially the same as the rotation axis to allow the probe body to turn about the rotation axis without causing the focus to move relative to the target;
    wherein the treatment probe has an imaging mode in which the imaging transducer has an imaging plane that contains the acoustic axis of the treatment transducer as located in the treatment mode to allow the probe body to turn about the rotation axis while the target remains in the imaging plane; and
    wherein the treatment probe is arranged to allow moving the probe body exclusively by rotation around the rotation axis.

2. The probe according to claim 1, wherein the treatment transducer is moveably mounted in the probe body.

3. The probe according to claim 2, wherein the treatment transducer is rotatably mounted in the probe body.

4. The probe according to claim 3, wherein the treatment transducer rotates, about an axis perpendicular to the rotation axis of the probe body.

5. The probe according to claim 1, wherein the imaging transducer is moveably mounted in the probe body.

6. The probe according to claim 5, wherein the imaging transducer is configured for translating in the probe body.

7. The probe according to claim 6, wherein the imaging transducer is configured for translating along a direction parallel to the rotation axis of the probe body.

8. The probe according to claim 1, wherein the imaging transducer is an array carrying out a linear scan.

9. The probe according to claim 8, wherein the imaging transducer comprises a linear scan axis, the linear scan axis being parallel to a longitudinal direction of the treatment transducer.

10. The probe according to claim 1, wherein the imaging transducer is integrated in the treatment transducer.

11. The probe according to claim 1, including a support on which the probe is mounted for rotation, the support translationally displacing the probe in a plane perpendicular to the rotation axis.

12. The probe according to claim 11, wherein the support translationally displaces the probe following the direction of the rotation axis.

13. The probe according to claim 11, wherein the support has a ball-and-socket joint for orientation of the probe.

14. The probe according to claim 11, wherein the support has an arch along which the probe moves.

15. The probe according to claim 14, wherein the radius of the arch is substantially equal to the distance between the arch and the focus of the treatment transducer.

16. The probe according to claim 1, wherein the first direction comprises a transverse direction of the treatment transducer and the second direction comprises a longitudinal direction of the treatment transducer.

17. The probe according to claim 1, wherein;
    an end of the probe body is formed by a balloon that is flexible and transparent to ultrasound, the balloon being adapted to be inflated by an ultrasound-transparent coupling fluid, and
    the balloon rests on a rigid contour symmetrical with respect to the acoustic axis of the treatment transducer, the inflated balloon having a foremost point which is substantially on the acoustic axis.

18. The probe according to claim 17, wherein the inflated balloon has a shape that is symmetrical with respect to the acoustic axis.

19. The probe according to claim 18, wherein:
    the probe body is not symmetrical with respect to a plane containing the rotation axis of the probe body and a longitudinal direction of the treatment transducer; and
    the rigid contour on which the balloon rests is defined by the edges of the probe body and by a cover.

20. An ultrasound treatment apparatus, comprising:
    a treatment probe for coagulating a target by applying focused ultrasound at a target, comprising:
        a probe body mounted for rotation about a rotation axis, the probe body carrying a treatment transducer and an imaging transducer;
        the treatment transducer being configured for emitting focused ultrasound along an acoustic axis towards a focus, in which the focused ultrasound forms a cone, having an apex, said apex being the focus and the cone having an angle at the apex which is less open in a first direction of the treatment transducer than in a second direction of the treatment transducer; and
        the imaging transducer being configured for obtaining an image of the target;
        wherein the treatment probe has a treatment mode in which the acoustic axis of the treatment transducer is substantially the same as the rotation axis to allow the probe body to turn about the rotation axis without causing the focus to move relative to the target;
        wherein the treatment probe has an imaging mode in which the imaging transducer has an imaging plane that contains the acoustic axis of the treatment transducer as located in the treatment mode to allow the probe body to turn about the rotation axis while the target remains in the imaging plane; and wherein the treatment probe is arranged to allow moving the probe body exclusively by rotation about the rotation axis;

said ultrasound treatment apparatus further comprising:

a screen allowing images obtained by the imaging transducer of the probe to be viewed;

means for symbolizing, on the screen, the treatment transducer of the probe, and the target to be treated;

means for entering limits of the target; and a computer configured for controlling treatment.

21. The ultrasound treatment apparatus according to claim 20, in which said first circuit is adapted to symbolize on the screen said acoustic beam as located during treatment, at a point in time when the treatment probe has an orientation transverse to that at the time of treatment.

22. A treatment probe for coagulating a target by applying focused ultrasound at a target, comprising:

a probe body mounted for rotation about a rotation axis, the probe body carrying a treatment transducer and an imaging transducer;

the treatment transducer being elongated in shape and configured to coagulate the target by emitting focused ultrasound along an acoustic axis towards a focus; and the imaging transducer configured for obtaining an image of the target;

wherein the treatment probe has a treatment mode in which the acoustic axis of the treatment transducer is substantially the same as the rotation axis to allow the probe body to turn about the rotation axis without causing the focus to move relative to the target;

wherein the treatment probe has an imaging mode in which the imaging transducer has an imaging plane that contains the acoustic axis of the treatment transducer as located in the treatment mode to allow the probe body to turn about the rotation axis while the target remains in the imaging plane; and wherein the treatment probe is arranged to allow moving the probe body exclusively about the rotation axis.

23. The probe according to claim 22, wherein the treatment transducer has an emitting surface with a longitudinal dimension and a transverse dimension and an aspect ratio between the longitudinal dimension and the transverse dimension which is greater than 1.2.

24. The probe according to claim 22, wherein the treatment transducer has an emitting surface with a longitudinal dimension and a transverse dimension and an aspect ratio between the longitudinal dimension and the transverse dimension smaller than 2.5.

25. The probe according to claim 22, wherein the treatment transducer has an emitting surface with a longitudinal dimension and a transverse dimension and an aspect ratio between the longitudinal dimension and the transverse dimension greater than 1.2 and smaller than 2.5.

* * * * *